United States Patent [19]
Greenspon et al.

[11] Patent Number: 5,954,661
[45] Date of Patent: Sep. 21, 1999

[54] TISSUE CHARACTERIZATION AND TREATMENT USING PACING

[75] Inventors: Arnold J. Greenspon, Elkins Park, Pa.; David K. Swanson, Mountain View; Dorin Panescu, Sunnyvale, both of Calif.; Steve S. Hsu, Columbia, S.C.; James G. Whayne, Saratoga, Calif.

[73] Assignees: Thomas Jefferson University, Philadelphia, Pa.; Boston Scientific Corporation, Natick, Mass.

[21] Appl. No.: 08/831,489

[22] Filed: Mar. 31, 1997

[51] Int. Cl.$^6$ ........................................................ A61B 5/04
[52] U.S. Cl. ................................................................. 600/510
[58] Field of Search ................................ 607/9, 510, 515, 607/518

[56] References Cited

U.S. PATENT DOCUMENTS

| | | | |
|---|---|---|---|
| 4,673,563 | 6/1987 | Berne et al. | 424/9.1 |
| 5,546,940 | 8/1996 | Panescu et al. | 128/642 |
| 5,577,509 | 11/1996 | Panescu et al. | 128/696 |
| 5,582,609 | 12/1996 | Swanson et al. | 606/39 |
| 5,595,183 | 1/1997 | Swanson et al. | 128/697 |
| 5,598,848 | 2/1997 | Swanson et al. | 128/696 |
| 5,601,088 | 2/1997 | Swanson et al. | 128/697 |

OTHER PUBLICATIONS

Goyal, R. et al. "Effect of coupling interval and pacing cycle length on morphology of paced ventricular complexes. Implications for pace mapping." Medline Accession No. 97096087, see entire abstract, 1997.

Goyal, R. et al. "Effect of isoproterenol on QRS complex morphology during ventricular pacing: Implication for pace mapping." BIOSIS Accession No. 98:253323, see entire abstract, 1998.

"Entrainment Techniques for Mapping Atrial and Ventricular Tachycardias", by Stevenson et al., Journal of Cardiovascular Electrophysiology, vol. 6, pp. 201–216.

"Identification Of Reentry Circuit Sites During Catheter Mapping And Radiofrequency Ablation Of Ventricular Tachycardia Late After Myocardial Infaction", by Stevenson et al., Circulation from the Divisions of Cardiology, UCLA School of Medicine, vol. 88, No. 4, Part 1, Oct. 1993.

"Radiofrequency Catheter Ablation of Ectopic Atrial Tachycardia Using Paced Activation Sequence Mapping", by Tracy et al., Journal of the American College of Cardiology, vol. 21, No. 4, Mar. 15, 1993, pp. 910–917.

"Catheter Ablation of Ventricular Tachycardia Related to Coronary Heart Disease", by Dubec et al, Hopital du Sacre Coer de Montreal and Department of Medicine, and Institut de Genie Biomedical, vol. 87, No. 2, Feb. 1993, pp. –649–651.

"Endocardial Activation Mapping and Endocardial Pace–Mapping Using a Balloon Apparatus", by Fann et al., The American Journal of Cardiology, vol. 55, Apr. 1, 1995, pp.–1076–1083.

"Holter Triage Ambulatory ECG Analysis", Cooper et al., Journal of Electrocaridology, vol. 29, No. 1, Jan. 1996, pp.–33–38.

IEEE Transactions on Biomedical Engineering, vol. 42, No. 7, Jul. 1995, "On the Detection of QRS Variations in the ECG", by Shaw et al., pp.–736–741.

*Primary Examiner*—Jeffrey R. Jastrzab
*Attorney, Agent, or Firm*—Lyon & Lyon LLP

[57] ABSTRACT

Heart tissue is characterized by using pacing without inducing ventricular tachycardia (VT). With the tissue characterization, a patient's risk of developing VT can be determined and a slow conduction zone in the patient's heart can be determined. The characterization involves applying pacing signals with varying pacing cycle intervals to a chamber of the patient's heart to pace the patient's heart. The response signals generated by the paced heart are received and used as the basis for characterizing the patient's heart tissue.

28 Claims, 6 Drawing Sheets

TISSUE CHARACTERIZATION AND TREATMENT USING PACING

TECHNICAL FIELD

This invention relates to the use of pacing to characterize tissue and, more particularly, to heart tissue characterization and treatment of heart tissue using pacing without inducing ventricular tachycardia.

BACKGROUND INFORMATION

A normal heartbeat involves generation of an electrical impulse and propagation of the electrical impulse across the heart, which causes each chamber of the heart to appropriately contract. Sometimes aberrant conductive pathways develop in heart tissues, and these disrupt the normal path of the electrical impulse. For example, anatomical obstacles or conduction blocks in heart tissue can disrupt the normal propagation of an impulse by causing the impulse to degenerate into several circular wavelets that circulate about the obstacles, thus disrupting normal activation within the heart tissue and chambers. Slow conduction zones in animal and human hearts constrained by anatomical or conduction blocks are believed to exist. Such a zone is a localized region of the heart tissue which propagates an impulse at a slower speed than normal heart tissue thus sometimes resulting in errant, circular propagation patterns or reentrant pathways. Reentrant pathways can result in an arrhythmia from the re-excitation of a region of cardiac tissue by a single impulse, and the arrhythmia continues for one or more cycles and sometimes results in tachycardia. Re-entrant ventricular tachycardia (VT) is an abnormally rapid ventricular rhythm with aberrant ventricular excitation (wide QRS complexes), usually in excess of 150 per minute, which is generated within the ventricle of the heart as a result of a reentrant pathway.

To treat VT, it is desirable first to determine the physical location of the source(s) of the aberrant pathways. Once located, the heart tissue can be destroyed by heat, chemicals, RF ablation, and/or other means. Ablation can remove the aberrant conductive pathway, restoring normal myocardial contraction. More specifically, to treat VT, the slow conduction zone must be located and destroyed or partially destroyed, with the goal of eliminating the slow conduction zone's ability to conduct electrical impulses.

It is known for physicians to examine the propagation of electrical impulses in heart tissue to locate aberrant conductive pathways. The techniques used to analyze these pathways, commonly called "mapping," identify tissue which can be ablated to treat the arrhythmia.

One form of conventional cardiac tissue mapping techniques uses multiple electrodes positioned in contact with epicardial heart tissue to obtain multiple electrograms. The physician stimulates myocardial tissue by introducing pacing signals through one or more (e.g., a pair) of electrodes and visually observes the morphologies of the electrograms recorded during pacing to determine activation times of electrograms at various epicardial locations. ("Pacing" means artificially stimulating the heart with one or more electrical signals.) Electrogram morphology refers to the shape of the electrical signals recorded from electrodes placed in the heart. This conventional mapping technique requires invasive open heart surgical techniques to position the electrodes on the epicardial surface of the heart. Furthermore, conventional cardiac tissue mapping techniques used for detecting local electrical events in heart tissues are often unable to interpret electrograms with multiple morphologies. Such electrograms are encountered, for example, when mapping a heart undergoing ventricular tachycardia (VT). For these reasons, consistent identification of foci cannot be achieved with current multi-electrode mapping technologies.

An improvement to conventional multiple-electrode cardiac tissue mapping techniques is disclosed in U.S. Pat. No. 5,577,509 which is incorporated in its entirety by reference. A minimally invasive basket catheter or multi-electrode structure is used as the electrodes for pacing and monitoring the heart such that open heart surgery is not required. Despite this improvement, this technique is less than ideal because the technique for choosing the earliest activation times necessary to produce the isochronal displays has not been perfected.

Another form of conventional cardiac tissue mapping techniques, called pace mapping, uses a roving electrode in a heart chamber for pacing the heart at various endocardial locations. The heart is monitored during pacing and electrocardiograms that are produced are compared to electrocardiograms produced during VT. VT may have been induced or spontaneous. When a pacing signal is applied to a slow conduction zone, the excitation wavefront caused by the pacing signal gets caught in the same circular motion that results in the VT. Therefore, a large proportion of the electrocardiograms produced during pacing will have morphologies that match the electrograms recorded during VT. In searching for a slow conduction zone, the physician must visually compare all paced electrocardiograms to those previously recorded during VT. The physician must constantly relocate the roving electrode to a new location to systematically map the endocardium. This pace-mapping technique is complicated and time consuming. It requires repeated manipulation and movement of the pacing electrode. At the same time, it requires the physician visually to assimilate and interpret the electrocardiograms. Improvements to the conventional pace mapping procedure are described in U.S. Pat. No. 5,595,183 which is incorporated in its entirety by reference. This patent describes methods of automatically comparing the electrograms obtained during pacing at multiple sites to those taken during induced or spontaneous VT. This patent also describes methods to pace automatically at multiple sites in a sequence to identify rapidly and efficiently pacing sites that provide a good match of 12-lead ECGs obtained during pacing and during VT.

Entrainment mapping is another conventional cardiac tissue mapping technique used to identify potential ablation sites for curing VT. In this technique, VT is pace-induced, then pacing is initiated at cycle lengths a little shorter than the VT cycle length. In some cases, the beating of the heart can be captured by the pacing attempt. If the heart is successfully captured, the electrocardiograms (recorded by 12 lead body surface electrodes) can exhibit changes in the morphology of the QRS complex as the heart is captured. In other circumstances, there is little or no change in the QRS morphology. If the heart is captured without a change in QRS morphology, the result is called concealed entrainment. On the other hand, if the heart is captured with a change in electrocardiogram waveform, the result is described as entrainment with fusion. Successful ablation sites can be identified as they usually exhibit concealed entrainment, with some additional timing constraints. However, only about 30% of the ablation attempts at sites identified by this method cure the VT.

SUMMARY OF THE INVENTION

The invention relates to characterizing tissue. More specifically, it relates to characterizing heart tissue to determine, for example, those patients at risk of re-entrant ventricular tachycardia (VT) and/or to determine a zone of slow conduction in the ventricle of a patient's heart to allow that zone to be treated such that it will no longer conduct. The tissue characterization preferably is achieved through the use of pacing and preferably without inducing VT in the heart being paced, and it requires less time to complete than conventional techniques (which generally require several hours to complete).

In accordance with the invention, a slow conduction zone in a heart of a patient suffering from, or suspected of being at risk for, VT is identified by pacing the patient's heart at one or more rates without inducing VT and then evaluating the characteristics of the signals produced by the paced heart. In one embodiment, efficiency can be achieved by placing a multiple-electrode basket in a selected chamber of the heart (e.g., the ventricle) such that the various electrodes contact many different locations of the inner wall of the heart chamber. In a typical use, one of the basket electrodes is used as the pacing electrode and others of the electrodes that are physically away from the pacing electrode are used to record/monitor the resulting heart signals, and then a different electrode is used as the pacing electrode and further recording/monitoring is performed with away electrodes of the basket. The resulting signals are then analyzed, preferably with a computing or processing device such as an appropriately programmed personal computer, and various information is determined such as the location of a zone of slow conduction or the likelihood of this patient being at risk for VT. An ablation catheter could then be used to apply energy to the zone of slow conduction in order to ablate that area of the ventricle and destroy or inhibit its ability to conduct thereby eliminating the VT or the possibility of VT.

In one aspect, the invention involves a method for characterizing heart tissue by using pacing without inducing ventricular tachycardia (VT). With the tissue characterization of the invention, a patient's risk of developing VT can be determined and/or a slow conduction zone in the patient's heart can be determined. The characterization involves applying pacing signals with varying pacing cycle intervals to a chamber of the patient's heart to pace the patient's heart. The response signals generated by the paced heart are received and used as the basis for characterizing the patient's heart tissue.

In accordance with this aspect of the invention, the identification of risk and/or a slow conduction zone can involve determining durations of the response signals and using those durations (e.g., by forming a ratio or a difference) as the basis for making the identification(s). The identified slow conduction zone can be treated to inhibit electrical conduction by the zone and thereby eliminate the VT. Also, the pacing signals can have at least a first pacing cycle interval and a second pacing cycle interval wherein the first pacing cycle interval is shorter in time than the second pacing cycle interval. Each of the first and second pacing cycle intervals may be at least 20% shorter than a pacing cycle interval corresponding to a normal sinus rhythm. Each of the first and second pacing cycle intervals may be in the range of about 260 milliseconds (ms) to about 800 ms. In one embodiment, the fastest pacing cycle interval is in the range of about 260 ms to about 320 ms, or more preferably in the range of 280 ms to 300 ms. At least two electrodes can be placed in the heart's chamber and used to apply the pacing signals and receive the response signals from the paced heart. These electrodes can be deployed into the heart's chamber by one or more catheter devices. For example, an expanding basket catheter with a plurality of electrodes can be used to access the heart's chamber and deploy some or all of the electrodes into contact with the inner wall of the chamber.

In another aspect, the invention relates to a system for characterizing heart tissue by using pacing without inducing ventricular tachycardia (VT). The system includes a plurality of electrodes, a signal generator, and a recorder system. With the tissue characterization of the invention, a patient's risk of developing VT can be determined and/or a slow conduction zone in the patient's heart can be determined. The characterization involves using the electrodes and the signal generator to apply pacing signals with varying pacing cycle intervals to a chamber of the patient's heart to pace the patient's heart. The response signals generated by the paced heart are received and used by the recorder system as the basis for characterizing the patient's heart tissue.

In accordance with this other aspect of the invention, the system can make the identification of risk and/or a slow conduction zone by determining durations of the response signals and using those durations (e.g., by forming a ratio or a difference) as the basis for making the identification(s). The identified slow conduction zone can be treated with an ablation catheter to inhibit electrical conduction by the zone and thereby eliminate the VT. Also, the pacing signals can have at least a first pacing cycle interval and a second pacing cycle interval wherein the first pacing cycle interval is shorter in time than the second pacing cycle interval. Each of the first and second pacing cycle intervals may be in the range of about 260 milliseconds (ms) to about 800 ms. In one embodiment, the fastest pacing cycle interval is in the range of about 260 ms to about 320 ms, or more preferably in the range of 280 ms to 300 ms. The electrodes can be provided on a basket catheter having a plurality of circumferentially spaced splines for contacting circumferentially spaced endocardial region in the chamber of the heart wherein each of the splines includes at least one of the electrodes. The signal generator can include a computer controller for controlling pacing signal parameters, pacing cycle intervals, and the sequence of pacing signals applied to the heart via the electrodes. The recorder system can include a signal processor for analyzing the response signals to assess the patient's risk of developing ventricular tachycardia and/or identify the slow conduction zone in the patient's heart.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

In one embodiment, the present invention is useful for identifying a slow conduction zone in a patient's heart where the heart is suffering from re-entrant ventricular tachycardia (VT). In another embodiment, the invention relates to assessing a patient's risk of developing or experiencing re-entrant VT. According to the present invention, VT does not need to be induced during the heart monitoring process to determine zones of slow conduction or assess a patient's risk of suffering from spontaneous VT.

Figure 1:
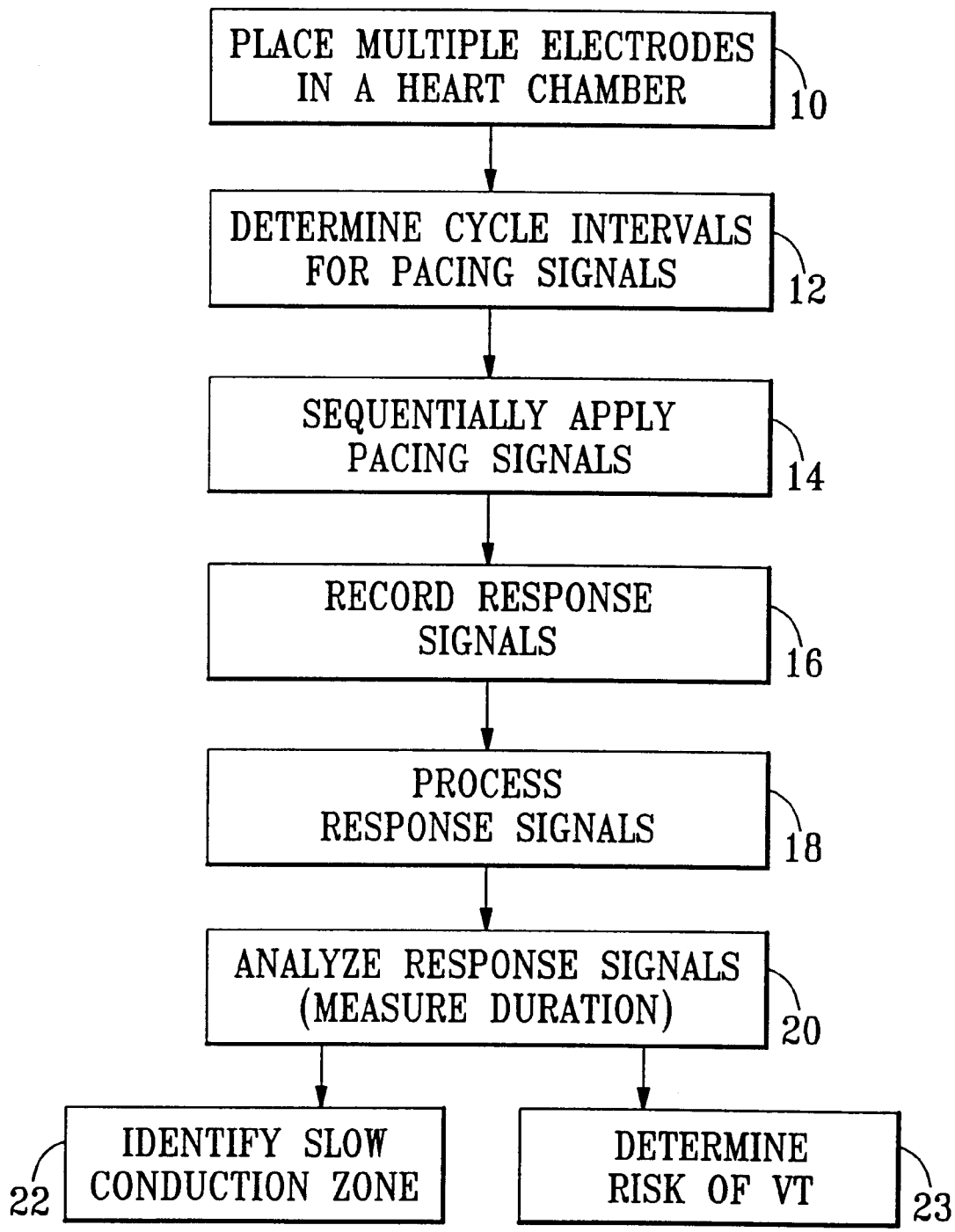
FIG. 1 is a flowchart of a method of identifying a slow conduction zone according to the invention.

Referring to FIG. 1, in accordance with an embodiment of the invention, multiple electrodes are placed in a selected chamber of a heart (an atrium or a ventricle) to allow the heart to be paced and monitored (step 10). The pacing and monitoring of the heart can be performed in order to identify a slow conduction zone in the heart chamber (step 22) or for the purpose of determining whether this patient is at risk of VT (step 23). In general, the invention relates to characterizing heart tissue using pacing. The electrodes are capable of sending pacing signals to the heart and receiving response signals from the paced heart. At least some of the electrodes are connected to a system for generating and sending pacing signals to the heart (i.e., a signal generator) and at least some of the electrodes are connected to a system for recording and processing the response signals from the paced heart (i.e., a recorder system). Pacing cycle intervals for the pacing signals to be applied to the heart are determined (step 12), and this information is conveyed to the signal generator. The signal generator and the recorder system could be housed in a single unit, or each could be contained in a separate unit. Pacing signals are sequentially applied to multiple locations in the heart chamber using at least some of the electrodes that are placed in the chamber (step 14). Response signals produced by the paced heart are recorded using the electrodes that are connected to the recorder system (step 16). The recorded signals may be processed to remove noise and to simplify electrogram duration measurement or to improve measurement accuracy (step 18). The processed signals are analyzed to determine a duration of each response signal generated by the paced heart (step 20). The durations of these signals are used to identify a slow conduction zone (step 22). Alternatively, the durations are used to determine a patient's risk of suffering from spontaneous VT(step 23). An appropriately programmed computer can be, and preferably is, used to perform the processing, analysis, and identification just described.

In a typical use, one of electrodes placed in the heart chamber is used as the pacing electrode and others of the electrodes that are physically away from the pacing electrode are used to record/monitor the resulting heart signals. Next, a different electrode is used as the pacing electrode and further recording/monitoring is performed with away electrodes. This can continue with various electrodes being used sequentially as the pacing electrode and others being used to record/monitor until enough information has been gathered about the heart under study to allow the desired result to be achieved, whether that is identifying a zone of slow conduction in the heart chamber, classifying the patient's heart as at risk for VT or not, or generally characterizing the heart tissue under study.

Figure 2:
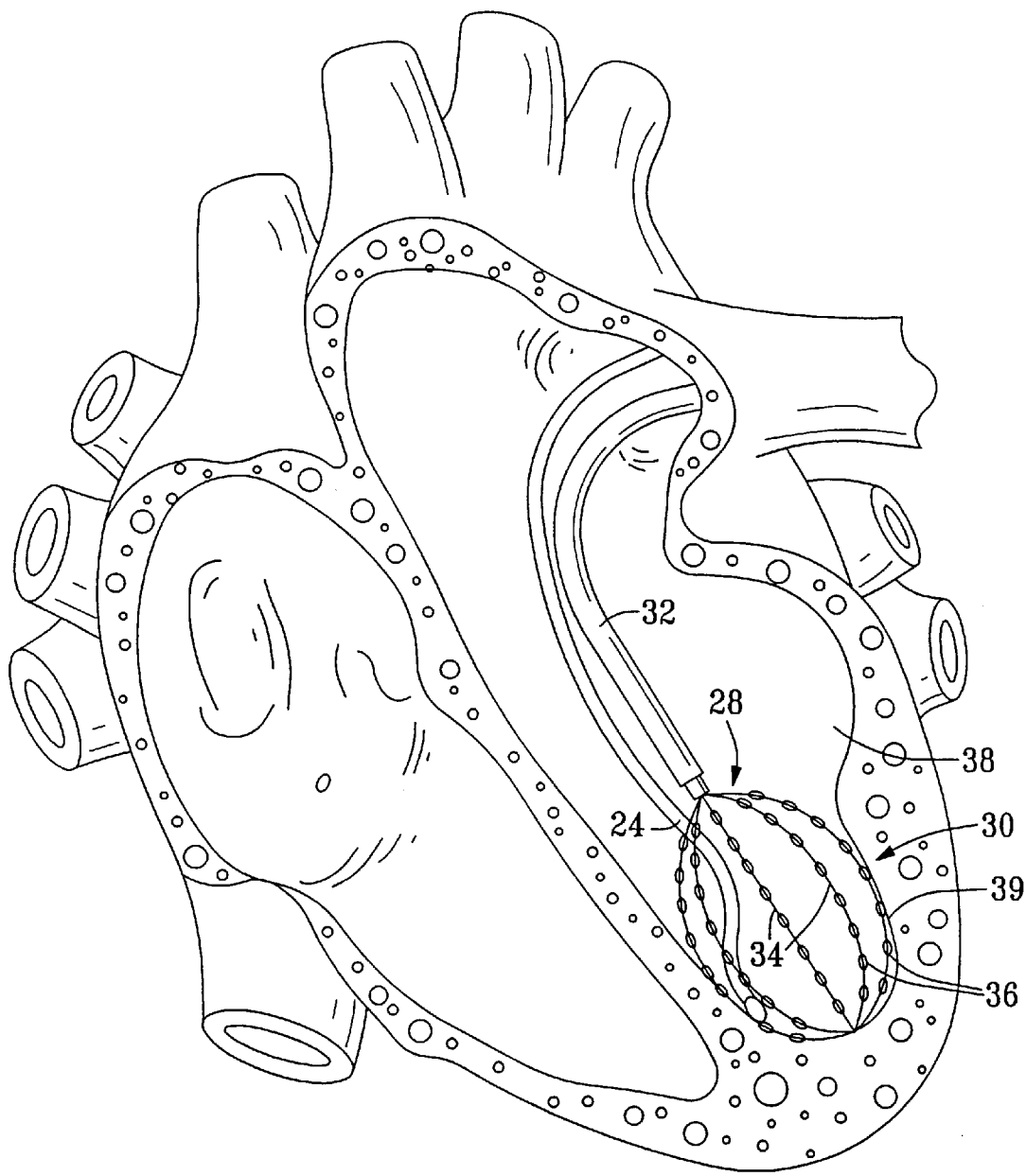
FIG. 2 is a diagram of a basket catheter disposed in a left ventricle of a heart.

The electrodes used with the present invention are any electrodes capable of sending and receiving electrical signals and being placed in a heart chamber. In one embodiment, a basket catheter described in U.S. Pat. No. 5,577,509 (which is incorporated in its entirety by reference) is deployed minimally invasively in a ventricle of the heart. Referring to FIG. 2, a basket catheter 28 comprises a flexible catheter tube 32 which carries a multiple-electrode support assembly 30. The multiple-electrode support assembly 30 comprises an array of flexible spline elements 34 assembled to form a three dimensional basket structure. The support assembly 30 retains the spline elements 34 in a circumferentially spaced array. The circumferentially spaced spline elements 34 make contact with a circumferentially spaced region of a heart chamber 38. The spline elements 34 carry an array of electrodes 36 for contacting the endocardial surface.

Figure 3:
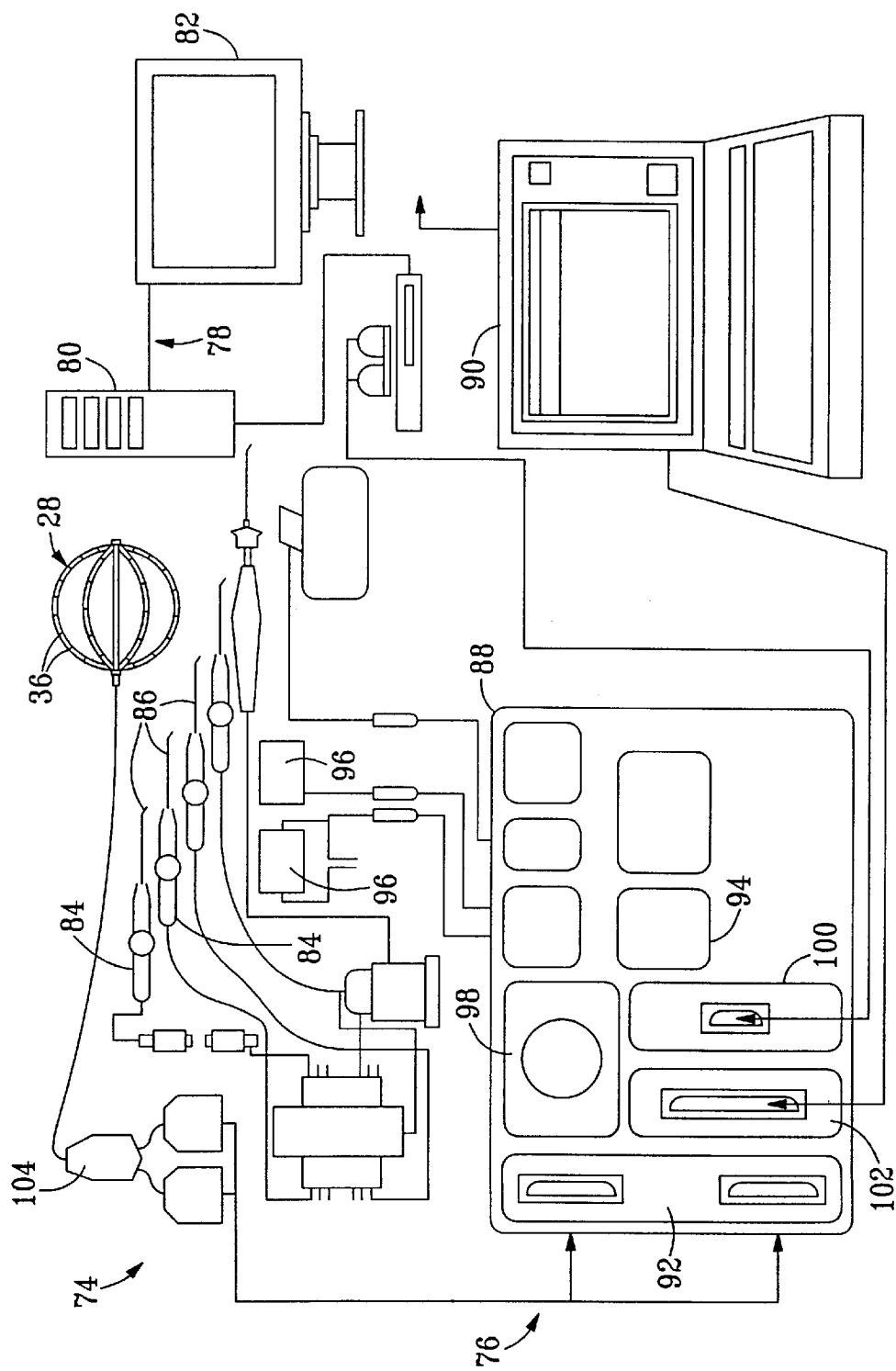
FIG. 3 is a block diagram of a signal generating and recording device.

Referring to FIG. 3, a basket catheter 28 is connected to a signal generating and recording device 74. In general, the signal generating and recording device 74 can be used to perform all of the generation, analysis, determination, identification, assessment, processing, etc. described herein. The device 74 includes an interfacing system 76 and a recorder system 78. The recorder system 78 includes a recording/processing unit 80 and a display unit 82 to record, store, analyze, and display signals acquired by the multiple electrodes 36 and other catheters 84 with electrodes 86, if there are any. The interfacing system 76 couples the multiple electrodes 36 to the recorder system 78 via an interface unit 88, enabling information acquired by the multiple electrodes 36 to be loaded into the recorder system 78. The interface unit 88 is coupled to a laptop computer 90. The interface unit 88 operates under the command of the laptop computer 90 to interconnect the electrodes 36 to the recorder system 78. The laptop 90 responds to requests and instructions entered onto its keyboard by an operator to switch among the electrodes 36 as required to achieve a desired function. The interface unit 88 has multiple input and output ports for connection to external devices. Port 92 is provided for connection to the catheter 28. Port 94 is provided for connection to external pacing pulse generator or stimulator 96. Pacing pulses generated by the external pacing pulse generator 96 can be selectively coupled to any of the electrodes 36. Port 98 permits connection to additional catheters 84. Port 100 provides for connection to the recorder system 78, and port 102 provides for connection to the laptop 90. The signal generating and recording device 74 also is described in pending U.S. patent application Ser. No. 08/770,971 which was filed on Dec. 20, 1996, which description is hereby incorporated by reference.

In one embodiment, an operator manually inputs pacing signal parameters including pacing cycle intervals and the sequence of electrode locations at which the pacing signals are applied into the signal generator 96. In another embodiment, the electrodes 36 are connected to a switching element 104. The switching element 104 enables automated (e.g., computer) control of the pacing signal parameters, pacing cycle intervals, and the sequence of electrode locations at which the pacing signals are applied. In a preferred embodiment, the signal generator 96 enables the operator to pace the heart from one of the electrodes 36, using either operator input or a computer algorithm selected by the operator. In a preferred embodiment, the signal has the capability to pace from each electrode of the multiple electrodes 36 in any sequential order. In addition, the signal generator 96 can pace the heart at a predetermined constant rate or at variable rates.

In one embodiment, all of the electrodes 36 of the basket catheter 28 are connected to the recorder system 78 to enable continuous recording from each electrode during the monitoring procedure. In another embodiment, only the electrodes not used in applying the pacing signals are connected to the recorder system 78 and used for monitoring. In a preferred embodiment, the recorder system 78 enables both unipolar recordings for any selected individual electrode and bipolar recordings for an electrode pair. In one embodiment, each electrogram complex which represents a response signal is automatically detected on all selected recording channels. The widths or duration of each electrogram complex also is automatically determined. In another embodiment, the system provides a review mode, within which the operator can edit many of the automated processing results, including electrogram detection and the time location of the leading and trailing edges of electrogram complexes.

After the electrodes 36 are placed in the selected chamber 38 of the heart and appropriately connected to the signal generator and recording device 74, an automated procedure that determines which electrodes 36 are in good electrical contact with the myocardium 39 may be initiated. Such an automated procedure is described in U.S. Pat. No. 5,598,848 which is incorporated in its entirety by reference. In one embodiment, electrical signals that activate the myocardium are emitted from one or more of the electrodes 36 and the resulting electrograms are detected to determine proper contact. The electrodes that are found to be in good electrical contact with the myocardium may be used to apply the pacing signals and to sense response signals.

A limited subset of the electrodes 36 that are in good contact with the myocardium 39 and located in differing regions of the chamber 38 are selected for use in pacing the heart. In one embodiment, a single electrode is chosen to pace a single location in the chamber 38. In another embodiment, one electrode 36 from each spline 34 is chosen. In yet another embodiment, electrodes 36 in positions A1, B2, C3, D4, E5, F6, G7, and H8 are used, where the letters designate each of eight splines and the numbers identify the electrodes on the spline with 1 being most distal and 8 being most proximal electrode on the spline 34.

Applying pacing signals at multiple locations of the chamber 38 provides several advantages. First, a slow conduction zone can be identified when pacing signals with short cycle intervals are applied at multiple locations in the heart, provided that pacing signals are applied to a relatively normal myocardium. Myocardium is the contractile tissue of the heart wall, more commonly called cardiac muscle. When pacing signals are applied at multiple locations, the likelihood that the pacing signals are applied at normal myocardium increases. Second, applying pacing signals at multiple locations also increases reliability because electrogram duration at a particular site is determined by analyzing multiple responses during the pacing procedure. This is because each electrode used for monitoring receives a response signal every time a pacing signal is applied. Since pacing signals are sequentially applied at multiple locations, each electrode receives multiple response signal, one from each location. Third, applying pacing signals at multiple locations allows variations in response signals due to difference in pacing locations to be determined.

Propagation velocity of the depolarization wave front or heart signals is direction dependent and the morphology of the electrogram recorded changes with the pacing site. The inventors of the present invention have discovered that the width or duration of the electrogram complex also varies with the pacing location. Therefore, variations in response signals resulting from multiple pacing locations may be useful in locating a slow conduction zone. Most commonly, the electrogram duration for each site is defined to be the longest duration measured at that site as the pacing location is varied. In an alternative analysis, the variation of electrogram durations measured at a single site as the pacing site is changed is used to identify an appropriate ablation site. The variation in measured electrogram duration can be either expressed as a percent of the mean, or can be expressed directly in milliseconds. Standard deviation is the preferred variation metric, but other means to quantify variation could be used such as, for example, the range or coefficient of variation.

Pacing cycle intervals for the pacing signals are determined before the pacing signals are applied. In one embodiment, pacing cycle intervals that are 20% shorter than the interval observed in a normal sinus rhythm are chosen. These pacing cycle intervals are approximately in the range from about 480 milliseconds (ms) to about 960 ms. In a preferred embodiment, the pacing cycle intervals are approximately in the range from about 260 ms to about 800 ms. The shortest pacing cycle interval is in the range of about 260 ms to about 320 ms, with a preferred range for the shortest pacing cycle interval being 280 ms to 300 ms. In one embodiment, a pacing signal with a single predetermined pacing interval is sequentially applied to each of several selected locations in the chamber. In another embodiment, multiple signals, with the same pacing intervals, are sequentially applied to each selected location in the chamber. In a preferred embodiment, at least eight pacing signals at the chosen pacing interval are applied to the first electrode location in the sequence prior to switching to the next electrode location in the sequence. One or more pacing signals are delivered to the other electrodes in the sequence. Although pacing multiple times at each location increases the time required to complete the pacing sequence, it provides more electrogram complexes or response signals to analyze and therefore improves measurement accuracy. When eight electrodes are used for pacing, the pacing sequence can be done relatively quickly. For example, at a pacing cycle length of 300 ms, if ten pacing signals are delivered at the first location, and four signals at each of the remaining seven locations, the sequence is completed in 11.1 seconds.

Alternatively, pacing signals with varying cycle intervals are applied to a single location or a sequence of locations. In one embodiment, the pacing signals may include a series of short cycle intervals followed by a series of normal sinus rhythm or longer cycle interval. A short cycle interval refers to an interval of less than about 400 ms. In another embodiment, the varying pacing cycle intervals includes a signal with a 600 ms interval, followed by a signal with a 300 ms interval, followed by a signal with a 400 ms cycle interval. If for each cycle interval, ten pacing pulses were delivered at the initial pacing site and four at the remaining sites, the entire pacing protocol for this phase could be completed in two minutes. Regardless of pacing intervals used, pacing signals may be monophasic, biphasic, or multiphasic.

The response signals generated by the paced heart are analyzed to determine which of the signals captured the myocardium or emanated from the selected electrode in response to the pacing signal. In a preferred embodiment, the final four signals delivered at the initial pacing location captures the myocardium, and all subsequent signals capture the heart. A continuous sequence of pulses that capture the heart simplifies such segment data analysis. However, even if one or two pacing pulses fail to capture the myocardium, the methods described in this invention are still valid, since multiple pacing signals are delivered to each selected electrode location. If none of the pacing signals captured the myocardium at a paced site, the pacing sequence should be repeated excluding the site at which pacing was unsuccessful. In one embodiment, an alternative site substitutes the unsuccessful site. In another embodiment, the unsuccessful site is simply eliminated from the pacing sequence.

The response signals from paced beats are analyzed to determine the beginning and the end of each response signal or electrogram complex in each recording channel. This information is used to determine both the propagation delay to each recording site and the electrogram duration at each recording site. The propagation delays to all or a subset of recording sites can be used to determine areas of slow conduction. Areas of slow conduction are identified by determining how fast the excitation wavefront is propagated. One system and method for automatically determining the propagation velocity of the excitation wavefront is described in U.S. Pat. No. 5,546,940, which is incorporated in its entirety by reference. The time from the pacing pulse to the beginning of the QRS complex on the standard ECG leads may be determined as well. That time interval, which can be referred to as the s-QRS interval, quantifies the time required for the excitation wavefront to propagate from the stimulation site to an exit site at which sufficient myocardial tissue is activated to be detected on the surface leads. An s-QRS interval of more than 10 ms implies that the stimulation site is in the slow conduction zone. An even longer s-QRS interval implies that the stimulation site is even further from an exit site (at least as expressed in conduction time).

Figure 4A:
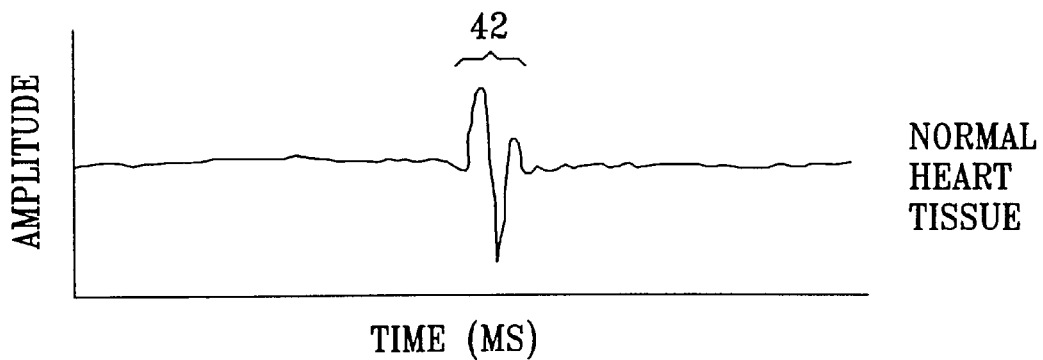
FIG. 4A is a graph showing normal heart tissue response to pacing.
Figure 4B:
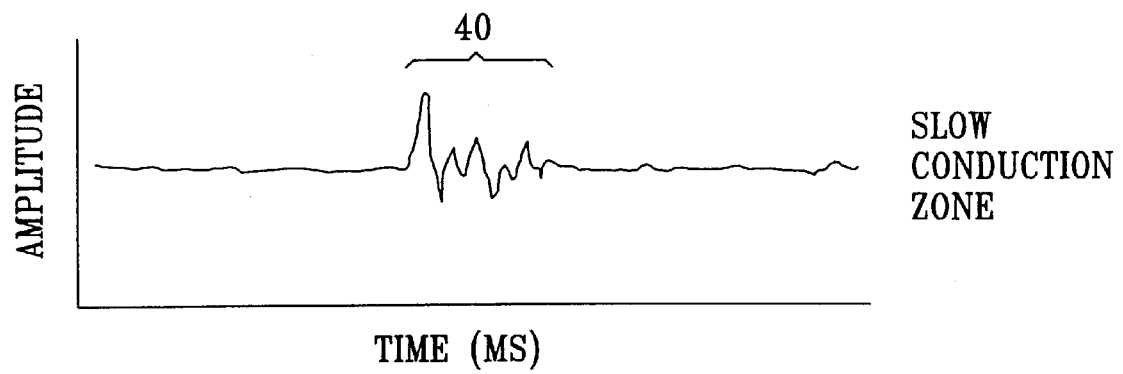
FIG. 4B is a graph showing the response to pacing of a slow conduction zone in the ventricle of a heart.

The duration information of each response signal electrogram complex can be used to identify a slow conduction zone or to identify a person's susceptibility to ventricular tachycardia. In one embodiment, the duration of each signal responding to fast pacing or pacing signals with short pacing cycle intervals are measured. Long duration may indicate susceptibility to VT. For example, in pigs, an electrogram duration of greater than 80 ms during rapid pacing with a pacing interval of 200 ms predicts susceptibility to VT. Referring to FIGS. 4A and 4B, a slow conduction zone produces an electrogram complex with a longer duration 40 than a normal zone 42 in response to fast pacing of the heart. In other embodiments, electrogram durations in response to fast and slow pacing at each location are analyzed. In one embodiment, the ratio of electrogram duration in response to fast pacing to electrogram duration in response to slow pacing is determined for each electrode location. A ratio greater than 1.5 indicates a slow conduction zone. In another embodiment, the difference between of the electrogram duration in response to fast pacing and the electrogram duration in response to slow pacing is determined for each electrode location. A difference of greater than 40 ms indicates a slow conduction zone. In yet another embodiment, pacing signals with sequentially increasing or decreasing cycle interval length are applied to a single location and electrogram durations in response to the pacing signals are examined for any exaggerated increase or decrease.

Figure 4C:
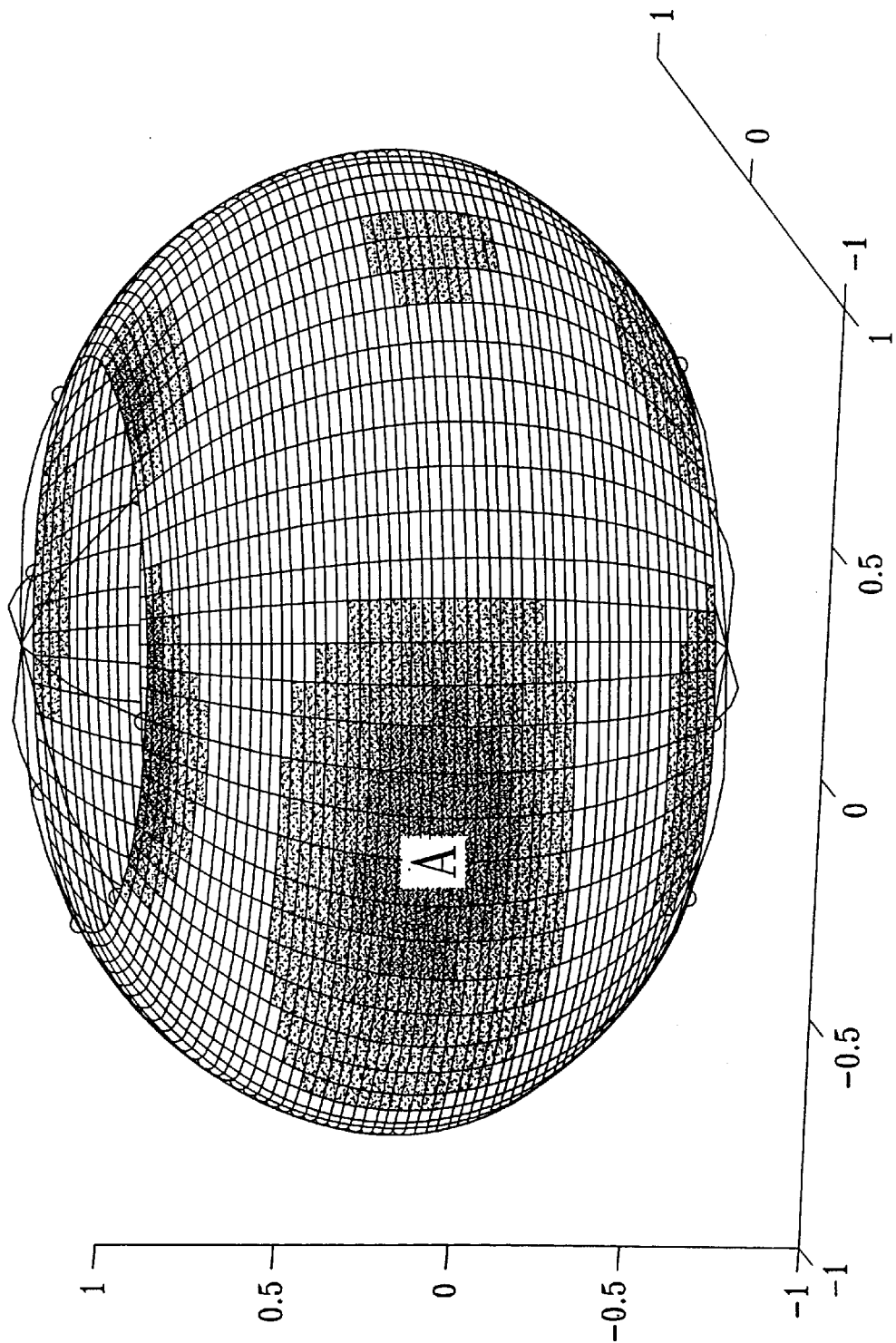
FIG. 4C is a 3-D display of electrograms of response signals.

The electrogram durations for each recording site can be coded and displayed graphically. In one embodiment, the display of electrogram durations is shown in a 3-D display, as a shaded 3-D model (see FIG. 4C). In another embodiment, the 3-D display may be shown as a wire frame representative. Details of 3-D display methods are described in U.S. Pat. No. 5,546,940 which is incorporated in its entirety by reference. In another embodiment, recording sites are simply sorted in order of electrogram duration as a means of easily identifying sites with long electrogram durations.

Both automatic and manual determinations of electrogram durations generally require the identification of the electrogram complexes in each recording channel before measuring or estimating their width or duration. Automatic detection of biological signal complexes with short durations and fast repetition rates has been studied and reported in both scientific publications and in patent disclosures. Also, signal processing of electrograms including ECGs (electrocardiograms), EEGs, and other biological signals generally is well-known. Two publications related to automatic methods for detecting the ECG waveform are: (1) "Holter triage ambulatory ECG analysis: Accuracy and time efficiency," Cooper et al., *J. Electrocardiol.*, 1(1), pp. 33–38, 1996; and (2) "On the detection of QRS variations in the ECG," Shaw et al., *IEEE Trans Biomed Eng.*, 42(7), pp. 736–741, 1995.

In general, all electrogram complexes have multiple peaks and zero crossings. A duration of a signal or an electrogram is defined herein to mean the time from the first "significant" deviation from the recording baseline to time at which no further "significant" deviation is observed. This definition of electrogram duration results in a non-stationary value for duration as noise is added to the system. That is, the duration becomes shorter as the signal is corrupted by more noise. For normal electrogram recordings, noise is small compared to the electrogram signal, resulting in duration determinations very close to those that would be obtained in a noise-free environment. For fractionated electrograms which are likely to result from a slow conduction zone, however, noise is significant. See for example FIG. 4B. Therefore, signals with as low a noise level as possible is sought, and signal processing is applied to reduce the effects of noise in accordance with the invention.

In general, the determination of electrogram duration is most difficult when the measurement is most important and interesting. This is when the duration is abnormally long, which may indicate a slow conduction zone. Long-duration complexes typically have many zero crossing and peak amplitudes which vary widely. Typically, an electrogram complex begins with one or more prominent peaks, followed by smaller variable-sized peaks. In some cases, trailing peaks can be similar in size to noise in the signal. In such cases, defining the end of the complex can be difficult, or even arbitrary. Pre-systolic activity can also be sensed, making the determination of the beginning of a complex even more difficult.

Signal processing can improve the accuracy of the duration measurement. In one embodiment, where the heart is stimulated multiple times under the same condition, ensemble averaging is used to improve the effective signal-to-noise ratio. For example, if the heart is paced four times, fiducial points (i.e., identifiable features in a complex that are used as time references) for four complexes from each recording can be aligned and used to ensemble average four beats from each channel, thereby increasing the signal-to-noise level by a factor of two in each channel.

Figure 5:
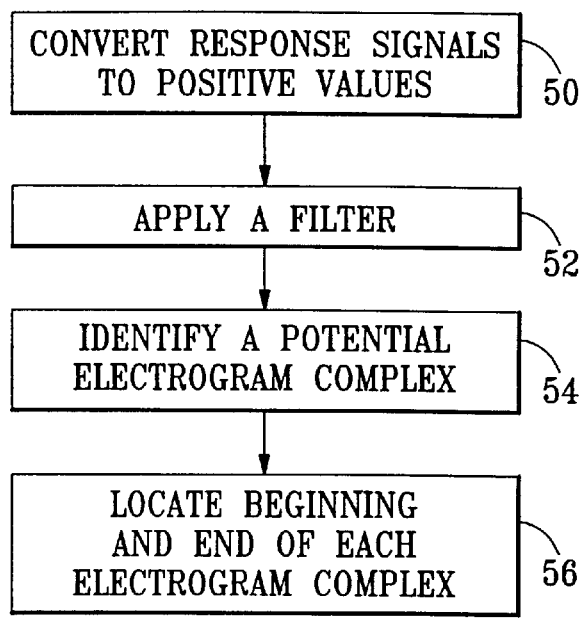
FIG. 5 is a flowchart of a method of determining a duration of a pacing response signal from a heart.

According to the invention, a more accurate electrogram duration can be determined by processing the response signals. Referring to FIG. 5, the response signals are first converted into positive values by applying, for example, a squaring or an absolute value function (step 50). A filter then is applied to the converted signals (step 52). In one embodiment, a median filter is applied to the resulting signals. With a median filter, the boxcar width is less than half the width of the narrowest expected electrogram. In a preferred embodiment, the width is between 10 ms and 20 ms. Applying a median filter greatly distorts the shape of the waveform of the electrogram, but leaves the width of the electrogram unmodified, provided that certain conditions are met. The most important of these conditions is that the magnitude of the signal level in the complex must be well above noise level more than half the time for all time intervals equal to the boxcar width. All signals with values above a threshold level are considered significant and become a part of an electrogram complex (step 54). One method of finding the beginning and end of the complex is to search backward and forward from the peak of the processed signal to find the first occurrences of signals below the threshold to find the beginning and end of the complex, respectively (step 56).

The threshold can be defined in various ways. In one embodiment, the threshold is defined in terms of percentage of the peak electrogram amplitude. In another embodiment, the threshold is defined as a fixed signal amplitude, such as 0.1 millivolt (mV). In a preferred embodiment, the threshold is defined as a value based on characteristics of the signal being recorded, i.e., an adaptive threshold. An adaptive threshold value may be the median value of all processed signal values that are not within the electrogram complex. If the electrogram duration is less than about 25% of the pacing cycle length, the median value for all processed signal values is commonly nearly the same as the median value of all non-complex processed signals. In this usual case, the median value for all processed signal values can be used for the threshold. This is the case since in normal tissue, most signals are near the iso-electric line, i.e., the signals are very small. In the above-described method, it is valuable to process the signal values for each heart beat separately, using signal segments from 1–1½ cycle lengths long. Signal segments including more than one complete cycle reduces the probability that the signal segment will begin or end in the middle of an electrogram complex. When relatively short signal segments are used for analysis (e.g. 1–1½ cycle lengths long), sorting the processed signal values in amplitude order, while maintaining pointers to the time location for each signal value, provides a simple means to implement the above-described method for determining electrogram duration. First, choose the median of the entire processed signal segment as the initial threshold. Then, use the time location of the largest signal to begin a forward and backward search in the processed signal for the beginning and end of the complex. If the complex duration is less than ¼ the cycle length, then stop. If the width of the complex is greater than ¼ the cycle length, redefine the threshold as the median of non-complex values and repeat the search. For longer complex durations, this iteration need not be done more than 2–3 times, since the solution rapidly converges. For each iteration step, the new threshold can be read directly from the original sorted file, since by definition, all values in the complex were above the original value for the threshold. In addition, if the beginning and ending locations were saved, the search for the newly-defined beginning and end of the complex can begin at the saved locations. Each iteration results in an increase or no change in measured electrogram duration. Other methods for defining the threshold value to determine the electrogram complex duration can be employed.

In another embodiment, the converted signals are processed with a low-pass filter (step 52). Low-pass filtering provides several benefits. This filtering process tends to decrease the effects of noise and removes near-zero values. The median filter is relatively tolerant to such low values. Electrogram durations will be biased to lower numbers without the low-pass filters. Also, if the median filter is chosen to be quite narrow, e.g. 5 ms, electrogram duration can be measured to be much shorter than it would be if measured manually by an expert electrophysiologist. Low-pass filtering tends to widen the processed signal. Therefore, if a box-car averaging method is used, the measured duration of the processed signal needs to be decreased by the width of the boxcar used for filtering. Various other low-pass filtering procedures may be used. For a given filter, however, the duration measured generally needs to be adjusted downward by the width of the filter's impulse response.

Any filtering that is performed generally will be accomplished by an appropriately programmed computer or dedicated hardware designed to perform one or more specific, desired signal processing/filtering functions.

Pacing artifacts can significantly complicate the task of automatically determining electrogram durations, especially for electrode pairs close to the pacing sites. This is because the pacing artifacts are temporally close to the beginning of the electrogram complex. There are several ways to overcome the interference of the pacing artifacts and to simplify the task of determining the beginning of each electrogram complex. In one embodiment, signals are recorded while pacing signals are applied and for 1 to 2 milliseconds after the termination of pacing signal application are ignored. Since the pacing artifact is propagated electrically, the pacing artifact is synchronous in all recording channels. Therefore, the most straightforward approach is simply to ignore all signals that are recorded during the pacing. In another embodiment, the effects of pacing artifacts can be reduced or eliminated entirely using either nonlinear or adaptive filtering techniques. These techniques are described in U.S. Pat. No. 5,601,088 which is incorporated in its entirety by reference. In yet another embodiment, response signals from electrodes located near the electrodes used in pacing are ignored. Since response signals from multiple locations are measured, it is possible to ignore some electrode locations. In another embodiment, response signals from electrodes that are used to apply the pacing signals are ignored. If the electrode is connected to the system for recording during pacing, the input amplifiers are saturated during and for some time after the pacing pulse has terminated. The time to recover from saturation varies by recorder system manufacturer and for different models of recorder systems produced by the same manufacturer. Even for systems with fast recovery from saturation, electrograms recorded from pacing electrodes tend to be greatly distorted for 10 ms to 100 ms after pacing due to after-potentials at the electrode-electrolyte interface following pacing. It thus is technically very difficult to obtain an accurate estimate of electrogram duration at a pacing site. In another embodiment, the recorder system is disconnected from all electrodes during the delivery of the pacing signals. For many recorder systems, this would eliminate the pacing artifacts in all recording channels, except for residual artifact signals due to after-potentials which is seen on all channels using the pacing electrode(s).

EXPERIMENTAL RESULTS

Figure 6:
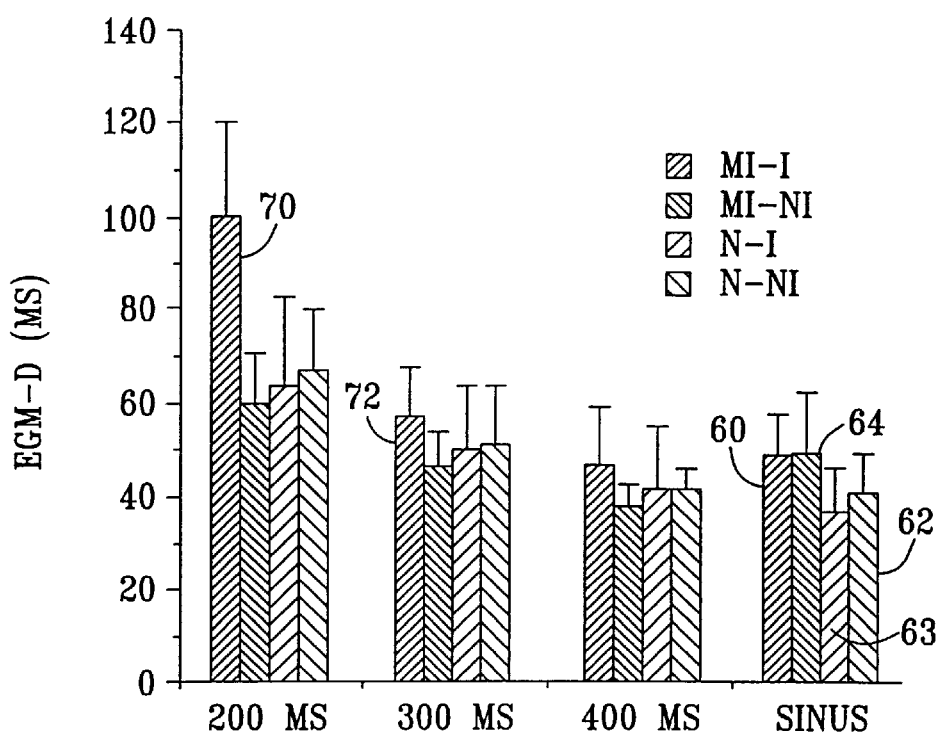
FIG. 6 is a graph showing various electrogram durations in response to various pacing rates.

The techniques of the present invention were used to predict inducibility of sustained VT in post-MI swines. Twenty-four swines were subjected to PTCA (percutaneous catheter ablation) balloon occlusion of the LAD (left anterior descending coronary artery) and injection of agarose gel beads and returned for programmed electrical stimulation four to six weeks later. Sixteen of the animals were inducible into sustained VT while eight were noninducible. Prior to programmed electrical stimulation, a basket catheter with sixty-four electrodes sold under the trademark Constellation™ by EP Technologies, Inc. of San Jose, Calif. was percutaneously inserted into the left ventricle for pacing the heart and recording the paced heart. Endocardial signals were recorded from thirty-two bipolar electrode pairs during sinus rhythm and pacing of the heart. Pacing signals with increasing cycle intervals from 200 ms to 400 ms were applied to the ventricle. Electrogram durations in response to pacing with incremental cycle intervals were analyzed and are shown in FIG. 6. During sinus rhythm, the electrode pair with longest duration and fractionation was identified as the MI zone 60, 64 while a pair of electrodes from the opposite side of the Constellation™ catheter was identified as a normal zone 62, 63. The electrogram duration in the MI zone 60, 64 was 49±9 ms which is significantly longer than in the normal zone 62, 63 where the duration was 39±9 ms. However, there was no difference in the electrogram duration between an animal inducible into VT (60, 63) and noninducible into VT (64, 62). Electrogram durations at these sites were analyzed during both sinus rhythm and during pacing at sites equi-distant from the MI zone and a normal zone. As the pacing rate increased, electrogram durations increased in both MI and normal zones. Prolongation of electrogram duration was particularly pronounced in the MI zone at rapid pacing rates 70, 72. Electrogram duration at a pacing cycle interval of 200 ms was 101±19 ms in animals inducible into VT (70). Electrogram duration of greater 80 ms during rapid pacing predicted inducibility of sustained VT with 90% sensitivity and 100% specificity. The experiment showed that prolongation of duration of a pacing-induced electrogram in the MI zone predicts inducibility of VT.

Based on these experimental results with pigs (FIG. 6), the techniques according to the invention apply to the human heart with the range of about 280 ms to about 300 ms being the fast pacing speed that will yield long-duration heart signal responses indicative of a slow conduction zone, the susceptibility of the heart to VT, and generally the character of the heart tissue. This ability to predict susceptibility of the heart to VT can be helpful to patients by giving them prior notice and a chance to undergo treatment before VT takes place.

The present invention also teaches treating VT. After a zone of slow conduction is identified according to the invention, it can be treated (e.g., ablated) to eliminate, or at least inhibit, its ability to conduct, thereby treating the VT. In one embodiment, some of the electrodes of the multiple electrodes used to apply pacing signals and to monitor the paced heart are also used to ablate the slow conduction zone. In the embodiment shown in FIG. 2, a separate ablation electrode 24 is inserted into the heart chamber 38 to ablate the slow conduction zone. This embodiment is described in U.S. Pat. No. 5,595,183, which is incorporated in its entirety by reference.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A method for characterizing heart tissue, comprising:
   (a) applying pacing signals with varying pacing cycle intervals to a chamber of a heart of a patient to pace the patient's heart without inducing ventricular tachycardia;
   (b) receiving response signals generated by the paced heart; and
   (c) characterizing the patient's heart tissue based on the response signals.

2. The method of claim 1 wherein step (a) comprises applying the pacing signals which have at least a first pacing cycle interval and a second pacing cycle interval wherein the first pacing cycle interval is shorter in time than the second pacing cycle interval.

3. The method of claim 2 wherein step (c) comprises identifying the patient's risk of developing ventricular tachycardia based on the response signals.

4. The method of claim 3 wherein the identifying step comprises:
   determining durations of the response signals; and
   assessing the patient's risk of developing ventricular tachycardia based on the durations of the response signals.

5. The method of claim 2 wherein step (c) comprises identifying a slow conduction zone in the patient's heart based on the response signals.

6. The method of claim 5 wherein the identifying step comprises:
   determining durations of the response signals; and
   identifying the slow conduction zone based on the durations of the response signals.

7. The method of claim 5 further comprising:
   treating the slow conduction zone to inhibit electrical conduction by the slow conduction zone.

8. The method of claim 7 wherein treating the slow conduction zone is by ablating the slow conduction zone.

9. The method of claim 2 wherein step (a) comprises applying the pacing signals in which each of the first and second pacing cycle intervals is at least 20% shorter than a pacing cycle interval corresponding to a normal sinus rhythm.

10. The method of claim 2 wherein step (a) comprises applying the pacing signals in which each of the first and second pacing cycle intervals is in the range of about 260 milliseconds to about 800 milliseconds.

11. The method of claim 2 wherein step (a) comprises applying the pacing signals in which one of the first and second pacing cycle intervals is in the range of about 260 milliseconds to about 320 milliseconds.

12. The method of claim 2 wherein step (c) comprises:
   determining durations of the response signals resulting from the pacing signals of the first pacing cycle interval and the pacing signals of the second pacing cycle interval;
   forming a ratio using the duration of at least one of the response signals resulting from the pacing signals of the first pacing cycle interval and the duration of at least one of the response signals resulting from the pacing signals of the second pacing cycle interval; and
   identifying the patient's risk of developing ventricular tachycardia based on the ratio.

13. The method of claim 2 wherein step (c) comprises:
   determining durations of the response signals resulting from the pacing signals of the first pacing cycle interval and the pacing signals of the second pacing cycle interval;
   forming a ratio using the duration of at least one of the response signals resulting from the pacing signals of the first pacing cycle interval and the duration of at least one of the response signals resulting from the pacing signals of the second pacing cycle interval; and identifying a slow conduction zone in the patient's heart based on the ratio.

14. The method of claim 2 wherein step (c) comprises:

determining durations of the response signals resulting from the pacing signals of the first pacing cycle interval and the pacing signals of the second pacing cycle interval;

forming a difference using the duration of at least one of the response signals resulting from the pacing signals of the first pacing cycle interval and the duration of at least one of the response signals resulting from the pacing signals of the second pacing cycle interval; and identifying the patient's risk of developing ventricular tachycardia based on the difference.

15. The method of claim 2 wherein step (c) comprises:

determining durations of the response signals resulting from the pacing signals of the first pacing cycle interval and the pacing signals of the second pacing cycle interval;

forming a difference using the duration of at least one of the response signals resulting from the pacing signals of the first pacing cycle interval and the duration of at least one of the response signals resulting from the pacing signals of the second pacing cycle interval; and identifying a slow conduction zone in the patient's heart based on the difference.

16. A method for characterizing heart tissue, comprising:

(a) placing at least two electrodes in a chamber of a heart of a patient;

(b) using at least one of the electrodes to apply sequentially pacing signals with predetermined varying pacing cycle intervals at multiple sites within the chamber to pace the heart without inducing ventricular tachycardia;

(c) using at least one of the electrodes to receive response signals produced by the paced heart; and (d) characterizing the patient's heart tissue based on the response signals.

17. The method of claim 16 wherein step (b) comprises applying the pacing signals which have at least a first pacing cycle interval and a second pacing cycle interval wherein the first pacing cycle interval is shorter in time than the second pacing cycle interval.

18. The method of claim 17 wherein step (d) comprises identifying the patient's risk of developing ventricular tachycardia based on the response signals.

19. The method of claim 18 wherein the identifying step comprises:

determining durations of the response signals; and assessing the patient's risk of developing ventricular tachycardia based on the durations of the response signals.

20. The method of claim 17 wherein step (d) comprises identifying a slow conduction zone in the patient's heart based on the response signals.

21. The method of claim 20 wherein the identifying step comprises:

determining durations of the response signals; and identifying the slow conduction zone based on the durations of the response signals.

22. The method of claim 20 further comprising:

treating the slow conduction zone to inhibit electrical conduction by the slow conduction zone.

23. A system for characterizing heart tissue, comprising:

a signal generator for use with a plurality of electrodes adapted for applying pacing signals to a chamber of a heart of a patient to pace the patient's heart, the signal generator also for generating and delivering to the heart via at least some of the electrodes pacing signals with varying pacing cycle intervals without inducing ventricular tachycardia in the patient's heart; and a recorder system for use with the plurality of electrodes and for receiving response signals generated by a paced heart and characterizing the patient's heart tissue based on the response signals.

24. The system of claim 23 further comprising a basket catheter comprising a plurality of circumferentially spaced splines for contacting circumferentially spaced endocardial region in the chamber of the heart, each of the splines including at least one of the plurality of electrodes.

25. The system of claim 23 wherein the signal generator includes a computer controller for controlling pacing signal parameters, pacing cycle intervals, and a sequence that the pacing signals are applied via the at least some of the electrodes.

26. The system of claim 23 wherein the recorder system comprises a signal processor for analyzing the response signals to assess the patient's risk of developing ventricular tachycardia.

27. The system of claim 23 wherein the recorder system comprises a signal processor for analyzing the response signals to identify a slow conduction zone in the patient's heart to produce an identification signal.

28. The system of claim 29 further comprising an ablation catheter and an ablation energy source, the ablation catheter being in electrical communication with the ablation energy source and the ablation catheter being adapted to treat an identified slow conduction zone to inhibit electrical conduction by the slow conduction zone in response to the identification signal.

* * * * *